United States Patent
Jones et al.

(10) Patent No.: US 6,306,619 B1
(45) Date of Patent: Oct. 23, 2001

(54) DEGP PERIPLASMIC PROTEASE A NEW ANTI-INFECTIVE TARGET AND AN IN VITRO ASSAY FOR DEGP PROTEASE FUNCTION

(75) Inventors: Hal C. Jones, Corvallis, OR (US); Christopher Liu, Cambridge, MA (US); Scott J. Hultgren, Town and Country, MO (US); Dennis E. Hruby; Christine A. Franke, both of Albany, OR (US); Amy K. Evans, West Linn, OR (US)

(73) Assignees: Washington University, St. Louis, MO (US); Siga Pharmaceuticals, New York, NY (US)

(*) Notice: Subject to any disclaimer, the term of this patent is extended or adjusted under 35 U.S.C. 154(b) by 0 days.

(21) Appl. No.: 09/605,858

(22) Filed: Jun. 29, 2000

Related U.S. Application Data
(60) Provisional application No. 60/140,990, filed on Jun. 29, 1999.

(51) Int. Cl.$^7$ .................................................. C12Q 1/37
(52) U.S. Cl. ............................................. 435/23; 435/220
(58) Field of Search .............................. 435/23, 24, 7.3, 435/32, 220, 184

(56) References Cited

PUBLICATIONS

Jones et al., "The Chaperone–Assisted Membrane Release and Folding Pathway is Sensed by Two Signal Transduction Systems", *The EMBRO Journal* vol. 16, No. 21, pp. 6394–6406 (1997).
(Pallen, M.J. and Wren, B.W. (1997) *Mol. Microbiol.* 26,209–221; )
Miller, C.G. (1996) in *Escherichia coli and Salmonella Cellular and Molecular Biology* (Neidhardt, F.C., eds) pp. 938–954, ASM Press Washington D.C.).
Danese, P.N., et al. (1995) *Genes and Development* 9,387–398.
Danese, P.N. and Sihavy, T.J. (1997) *Genes Dev.* 11,1183–1193).
Strauch, K.L., Johnson, K. and Beckwith, J. (1989) *J. Bacteriol.* 171,2689–2696.
Strauch, K.L. and Beckwith, J. (1988) *Proc. Natl. Acad. Sci. U.S.A.* 85,1576–1580.
Lipinska, B., Sharma, S. and Georgopoulos (1988) *Nucleic Acids Research* 16,10053–10066.
Seol, J.H., et al. (1991) *Biochemical and Biophysical Research Communications* 176,730–736.
Lipinska, B., Zylicz, M. and Georgopoulos, C. (1990) *J. Bacteriol.* 172,1791–1797.
Skorko–Glonek, J., et al. (1995) *Gene* 163,47–52.
Kolmar, H., Waller, P.R.H. and Sauer, R.T. (1996) *J. Bacteriol.* 178,5925–5929.
Laskawska, E., et al. (1996) *Mol. Microbiol.* 22,555–571.
Johnson, K., et al. (1991) *Mol. Microbiol.* 5,401–407.
Elzer, P.H., et al. (1996) *Research in Veterinary Science* 60,48–50.
Elzer, P.H., et al. (1996) *Infection and Immunity* 64,4838–4841.
Li, S.–R., et al. (1996) *Infection and Immunity* 64,2088–2094.
Boucher et al., (1996) *J. Bacteriol.* 178,511–523.
Gasc, A–M et al. (1998) *Microbiology* 144:433–439.
Caverd, D., Lazdunski, C. and Howard, S.P. (1989) *J. Bacteriol.* 171,6316–6322.
Bakker, D., et al. (1991) *Mol. Microbiol.* 5,875–886.
Jones, C.H., et al. (1997) *EMBO J.* 16,6394–6406.
St. Geme III, J.W. and Grass, S. (1998) *Mol. Microbiol.* 27,617–630 Waller, P.R. and Sauer, R.T. (1996) *J. Bacteriol.* 178,1146–1153.
Levchenko, I., et al. (1997) *Cell* 91,939–947.
Hultgren, S.J., Normark, S. and Abraham, S.N. (1991) *Annu. Rev. Microbiol.* 45,383–415.
Hultgren, S.J., Jones, C.H. and Normark, S.N. (1996) in *Escherichia coli and Salmonella*; *Cellular and Molecular Biology* (Neidhardt, F.C., eds) pp. 2730–2756, ASM Press Washington DC.

*Primary Examiner*—Mary E. Mosher
(74) *Attorney, Agent, or Firm*—Burns, Doane, Swecker & Mathis, L.L.P.

(57) ABSTRACT

The DegP (HtrA) protease is a multifunctional protein essential for the removal of misfolded and aggregated proteins in the periplasm. The present invention provides an assay for inhibitors of DegP activity, comprising mixing a suspected inhibitor of DegP activity with DegP and a suitable substrate (preferably a native substrate of DegP such as PapA) and detecting changes in DegP activity. DegP has been shown to be essential for virulence in several Gram negative pathogens. Only three natural targets for DegP have been described: colicin A lysis protein (Cal), pilin subunits (K88, K99, Pap) and recently HMW1 and HMW2 from *Hemophilus influenzae*. In vitro, DegP has shown weak protease activity on casein and several other non-native substrates. The present inventors have identified the major pilin subunit of the Pap pilus, PapA, as a native DegP substrate and demonstrated binding and proteolysis of this substrate in vitro. Using an $NH_2$-terminal affinity tag the present inventors have purified PapA away from the PapD chaperone, in the presence of denaturant, to use as a proteolysis substrate. This finding will allow the identification of the DegP recognition and cleavage sites in substrate proteins, and further, allow the design of small molecule inhibitors of protease function.

8 Claims, 8 Drawing Sheets

FIG. 7A

DegP consensus comparison - Catalytic domain

```
                           108
Gram neg.  GSGVIx    (5)   GyxxTNNHVh   (5)   IxVxLxDG   (7)
Gram pos.  GSGVIY          xYIVTNNHVh         hxhxLxDG 138
Gram neg.  GxDxxxDhAhhxh   (13)   DS   (3)   VGD
Gram pos.  GxDxxSDhAVhxI          DS         hGE Gram neg.  hhAxGNPFGLxxTVTxGIVSAxGR   (10)
Gram pos.  hiAIGxPLGxxxTVTQGIVSxLXR Gram neg.  IQTDAAINxGNSGGxLxBxxGZhIGINT   (11)
Gram pos.  IQTDAAINPGNSGGxLxNxxGZhIGINS Gram neg.  GIGFAIPxN
Gram pos.  GhGFAIPSN
```

- PDZ = PSD95 - Postsynaptic density protein; Dlg-discs-larger protein; ZO-1-zona occludens-1
- Residues conserved in >60% of sequences are shown
- B = Asp or Asn; Z = Glu or Gln; x = any residue
- 36 Gram-negative and 5 Gram-positive sequences included
- The catalytic triad, His-Asp-Ser residues are underlined
- Sequence numbering is according to *E. coli* DegP
- The number of residues separating each sequence block is indicated in parentheses

FIG. 7B

Bacterial PDZ domain consensus

PDZ domain 1

| | | | | | |
|---|---|---|---|---|---|
| Gram neg. | GxVxRGxLGh | (4) | hxxhA | (10) | Gxxxxh (7) |
| Gram pos. | GxhxRPxLGh | (3) | BLxxh | (10) | hxhxxV (7) |
| | | | | | |
| Gram neg. | SPAxKAGhxxGDVIxxhNGxxh | (5) | Lxxxh | (5) | |
| Gram pos. | xxAAxxGLKxxDVIxxhDGKxh | (5) | LxxxhLYxH | (5) | |

Gram neg. GxxhxLxhhR
Gram pos. xDThxhxxxR

PDZ domain 2

Gram neg. GxxGA (9) Ghhxxh (4) PAAxxG (3)
GdhhhxhNxWphxxhxxhxxL (5) hhhLhxR

- PDZ = PSD95 - Postsynaptic density protein; Dlg-discs-larger protein; ZO-1-zona occludens-1
- Residues conserved in >60% of sequences are shown
- Lower case letters indicate residues conserved in >50% of sequences
- h = Ala, Leu, Ile, Val; B = Asp or Asn; x = any residue
- 36 Gram-negative sequences included; 5 Gram-positive sequences included
- Gram-positive DegP homologs do not have a 2$^{nd}$ PDZ domain
- The first PDZ domain starts approximately 50-70 residues after the conserved serine of the catalytic triad
- The number of residues separating each sequence block is indicated in parentheses

FIGURE 8

```
              1    .    .    .    .    .    10   .    .    .    .    .    20   .    .    .    .    .    30   .    .    .    .    .    40   .    .    .    .    .    50
E. coli htrA  .    .    .    .    M    K    K    T    T    L    .    A    L    S    R    L    A    L    S    L    G    .    L    A    L    S    P    L    S    A    T    A    .    A    E    T    S    S    A    T    T    A    Q    .    Q    M    P    S    L    A    P    M    L    E
S,aureushtrA  -    -    -    -    -    -    -    -    -    -    -    -    -    -    -    -    -    -    -    -    -    -    -    -    -    -    -    -    -    -    -    -    -    -    -    -    -    -    -    -    -    -    -    -    -    -    -    -    -    -    -    -    -    -
S.pneum.htrA  M    E    A    N    M    K    H    L    K    T    .    F    Y    K    K    W    F    Q    L    L    V    .    V    I    V    I    S    F    F    S    G    A    .    L    G    S    F    S    I    T    Q    L    T    .    Q    K    S    S    V    N    N    S    N
s.pyog.htrA   -    -    -    -    M    P    .    .    .    .    .    S    M    K    H    I    L    K    S    L    S    .    I    L    L    I    G    F    L    G    G    L    .    I    A    I    I    T    F    N    N    L    Y    .    P    H    S    P    S    K    I    N    S    G 60                                  70                                  80                                  90                                  100
E. coli htrA  .    K    V    M    P    S    V    V    S    I    N    .    V    E    G    S    T    T    V    N    T    P    .    R    M    P    R    N    F    Q    Q    F    F    .    G    D    D    S    P    F    C    Q    E    G    .    S    P    F    Q    S    S    P    F    C    Q
S,aureushtrA  -    -    -    -    -    -    -    -    -    -    -    -    -    -    -    -    -    -    -    -    -    -    -    -    -    -    -    -    -    -    -    -    -    -    -    -    -    -    -    -    -    -    -    -    -    -    -    -    -    -    -    -    -    -    -
S.pneum.htrA  .    N    S    T    I    T    Q    T    A    Y    K    .    N    E    N    S    T    T    Q    A    V    N    .    K    V    K    D    A    V    V    S    V    I    .    T    Y    S    A    N    R    Q    N    -    -    .    -    -    -    S    V    F    G    -
s.pyog.htrA   .    K    A    T    T    S    N    M    V    F    N    .    N    T    T    N    T    T    K    A    V    K    .    A    V    Q    N    A    V    V    S    V    I    .    N    Y    Q    D    N    P    S    S    S    L    .    S    N    P    Y    T    K    L    F    G    E 110                                 120                                 130                                 140                                 150
E. coli htrA  .    G    G    Q    G    G    N    G    G    G    Q    .    Q    Q    K    F    M    A    L    G    S    G    .    V    I    I    D    A    D    K    G    -    .    Y    V    V    T    N    N    H    V    V    D    .    N    A    T    V    I    K    V    Q    L    S
S,aureushtrA  -    -    -    -    -    -    -    -    -    -    -    -    -    -    -    -    -    -    V    G    S    S    G    .    V    V    Y    K    K    S    G    D    T    L    .    Y    I    I    V    T    N    A    H    V    V    G    .    D    K    E    N    Q    K    I    T    F    S
S.pneum.htrA  .    -    -    N    D    D    T    D    T    D    .    S    Q    R    I    S    S    E    G    S    G    .    V    I    Y    K    K    N    D    K    E    A    .    Y    I    V    T    N    N    H    V    I    N    .    G    A    S    K    V    D    I    R    L    S
s.pyog.htrA   .    G    -    R    S    K    E    N    K    D    A    .    E    L    S    I    F    S    E    G    S    G    .    V    I    Y    R    K    D    G    N    S    A    .    Y    V    V    T    N    N    H    V    I    D    .    G    A    K    R    I    E    I    L    M    A 160                                 170                                 180                                 190                                 200
E. coli htrA  .    D    G    R    K    F    D    A    K    M    V    .    G    K    D    P    R    S    D    I    A    L    .    I    Q    I    Q    N    -    P    K    N    L    .    T    A    I    K    M    A    D    S    D    A    .    L    R    V    G    D    Y    T    V    G    I
S,aureushtrA  .    N    N    K    S    V    V    G    K    V    L    .    G    K    D    K    W    S    D    L    A    V    .    V    K    A    T    S    S    D    S    N    N    .    K    E    I    A    I    G    D    S    N    N    .    L    V    L    G    E    P    I    L    V    V
S.pneum.htrA  .    D    G    T    K    V    P    G    E    I    V    .    G    A    D    T    F    S    D    I    A    V    .    V    K    I    S    S    -    E    K    V    T    .    T    V    A    E    F    G    D    S    S    K    .    L    T    V    G    E    T    A    I    A    I
s.pyog.htrA   .    D    G    S    K    V    V    G    E    L    V    .    G    A    D    T    Y    S    D    L    A    V    .    V    K    I    S    S    -    D    K    I    K    .    T    V    A    E    F    A    D    S    T    K    .    L    N    V    G    E    V    A    I    A    I 210                                 220                                 230                                 240                                 250
E. coli htrA  .    G    N    P    F    G    -    -    L    G    E    .    T    V    T    S    G    I    V    S    A    L    .    G    R    S    G    L    N    A    E    N    Y    .    E    N    -    -    -    -    -    -    F    .    I    Q    T    D    A    A    I    N    R    G
S,aureushtrA  .    G    N    P    L    G    V    D    F    K    G    .    T    V    T    E    G    I    I    S    G    L    .    N    R    N    V    P    I    D    F    D    K    .    D    N    K    Y    D    M    L    M    K    A    .    F    Q    I    D    A    S    V    N    P    G
S.pneum.htrA  .    G    S    P    L    G    S    E    Y    A    N    .    T    V    T    Q    G    I    V    S    S    L    .    N    R    N    V    S    L    K    S    E    D    .    G    Q    -    -    A    I    S    T    K    A    .    I    Q    T    D    T    A    I    N    P    G
s.pyog.htrA   .    G    S    P    L    G    T    Q    Y    A    N    .    S    V    T    Q    G    I    V    S    S    L    .    S    R    T    V    T    L    K    N    E    N    .    G    E    -    -    T    V    S    T    N    A    .    I    Q    T    D    A    A    I    N    P    G
```

DEGP PERIPLASMIC PROTEASE A NEW ANTI-INFECTIVE TARGET AND AN IN VITRO ASSAY FOR DEGP PROTEASE FUNCTION

This application claims priority under 35 U.S.C. §§119 and/or 365 to Ser. No. 60/140,990 filed in U.S.A. on Jun. 29, 1999; the entire content of which is hereby incorporated by reference.

BACKGROUND OF THE INVENTION

1. Field of the Invention

The DegP (HtrA) protease is a multifunctional protein essential for the removal of misfolded and aggregated proteins in the periplasm. DegP has been shown to be essential for virulence in several Gram negative pathogens. Only three natural targets for DegP have been described: colicin A lysis protein (Cal), pilin subunits (K88, K99, Pap) and recently HMW1 and HMW2 from *Hemophilus influenzae*. In vitro, DegP has shown weak protease activity on casein and several other non-native substrates. The present inventors have identified the major pilin subunit of the Pap pilus, PapA, as a native DegP substrate and demonstrated binding and proteolysis of this substrate in vitro. Using an $NH_2$-terminal affinity tag the present inventors have purified PapA away from the PapD chaperone, in the presence of denaturant, to use as a proteolysis substrate. This finding will allow the identification of the DegP recognition and cleavage sites in substrate proteins, and further, allow the design of small molecule inhibitors of protease function.

2. Description of the Related Art

Proteolysis of misfolded and denatured proteins in the bacterial cytoplasm and periplasm is a crucial housekeeping function and critical for cell viability (Pallen, M. J. and Wren, B. W. (1997) *Mol. Microbiol.* 26,209–221; Miller, C. G. (1996) in *Escherichia coli and Salmonella Cellular and Molecular Biology* (Neidhardt, F. C., eds) pp. 938–954, ASM Press Washington D.C.). It is becoming increasingly clear that the proteolytic machinery is also an essential component for bacterial pathogenesis (Pallen & Wren, supra). Recently, scientists have uncovered a regulatory system, CpxA/CpxR, that responds to the changing environment of the periplasm; recruiting proteases, chaperones and "foldases" to assist in managing the state of affairs in this bacterial compartment (see, e.g., Danese, P. N., et al. (1995) *Genes and Development* 9,387–398; Danese, P. N. and Silhavy, T. J. (1997) *Genes Dev.* 11, 1183–1193). As the host often presents a hostile environment to the invading organism it is suggested that the CpxA/CpxR regulatory circuit is "tripped" upon engaging the host defenses. One of the most important proteases in the periplasm, the DegP/HtrA serine protease (Pallen & Wren, supra) is a member of the CpxA/CpxR regulon (Danese, P. N., et aL (1995), supra; Danese and Silhavy (1997) supra). This protein is also a key player in pathogenesis in Salmonella, Brucella, and Yersinia (Pallen & Wren, supra). Specifically, DegP has been shown to be a virulence determinant in *Salmonella typhimurium*, *Brucella abortus* and *Yersinia enterocolitica*. According to the current model of DegP function in pathogenesis, DegP acts to remove misfolded proteins and protein aggregates that result from exposure to reactive oxygen intermediates in the host. In the absence of functional DegP, these protein aggregates compromise the pathogenic process (Pallen & Wren, supra).

The DegP (degradation) nomenclature refers to the initial mapping of a mutation in *E. coli* that allowed the accumulation of unstable fusion proteins in the periplasm (Strauch, K. L., Johnson, K. and Beckwith, J. (1989) *J. Bacteriol.* 171,2689–2696; Strauch, K. L. and Beckwith, J. (1988) *Proc. Natl. Acad. Sci. U.S.A.* 85,1576–1580). The HtrA(heat shock regulated) designation indicates that a transposon insertion in the same gene resulted in a heat sensitive growth phenotype (Lipinska, B., Sharma, S. and Georgopoulos (1988) *Nucleic Acids Research* 16,10053–10066). Lastly, DegP was also designated protease Do, again as a mutation that conferred a heat sensitive phenotype in *E. coli* (Seol, J. H., et al. (1991) *Biochemical and Biophysical Research Communications* 176,730–736). DegP exhibited functional protease activity in in vitro assays using casein as a substrate, although its activity on this substrate was weak (Lipinska, B., Zylicz, M. and Georgopoulos, C. (1990) *J. Bacteriol* 172,1791–1797). Lipinska et al. demonstrated that the activity on casein was inhibitable by DFP and not by any other known protease inhibitors, suggesting that DegP is a serine protease. Site directed mutagenesis at serine 210 and histidine 105, two components of the serine protease catalytic triad, compromised DegP function in vitro and in vivo; i.e. strains carrying serine 210 or histidine 105 mutant derivatives were sensitive for growth at elevated temperatures (Skorko-Glonek, J., et al. (1995) *Gene* 163,47–52). The preferred substrate for DegP appears to be proteins that are globally or transiently denatured; suggesting that the role in vivo is to clear misfolded or denatured proteins from the periplasm (Kolmar, H., Waller, P. R. H. and Sauer, R. T. (1996) *J. Bacteriol* 178,5925–5929). In support of this finding, Laskowa et al. (Laskowska, E., et al. (1996) *Mol Microbiol.* 22,555–571) demonstrated in vitro that purified DegP protein would degrade thermally aggregated proteins fractionated from *E. coli* extracts and that the DnaJ chaperone would antagonize DegP degradation; i.e. the chaperone would aid in refolding the proteins such that they were no longer targets for degradation by DegP.

In addition to its weak protease activity, DegP/HtrA has been shown to be a virulence factor for several pathogenic organisms. In *Salmonella typhimurium*, htrA nulls were found to be avirulent and more susceptible to oxidative stress (Johnson, K., et al. (1991) *Mol. Microbiol.* 5,401–407). The authors of this study suggest that the htrA mutants are less able to withstand oxidative killing within the macrophage. An htrA lesion was found to be useful in attenuating *Salmonella typhi* for implementation as a vaccine strain. Similarly, *Brucella abortus* and *Brucella melentensis* htrA null mutants were attenuated for virulence in goats and found to be significantly more sensitive to oxidative killing by cultured neutrophils in vitro (Elzer, P. H., et al. (1996) *Research in Veterinary Science* 60,48–50; Elzer, P. H., et al. (1 996) *Infection and Immunity* 64,4838–4841; Phillips, R. W., et al. (1997) *Research in Veterinary Science* 63,165–167). An isogenic pair, wild-type and htrA null mutant, in *Yersinia enterocolitica* were created and tested in a mouse yersiniosis model. HtrA was found to be essential for virulence and the mutant strain was more sensitive to oxidative stress (Li, S.-R., et al. (1996) *Infection and Immunity* 64,2088–2094). Finally, Boucher et al. ((1996) *J. Bacteriol.* 178,511–523) recently demonstrated that *Pseudomonas aeruginosa* conversion to mucoidy, the so-called CF phenotype involves two HtrA homologs. DegP homologs have been found in *Streptococcus pneumoniae* (Gasc, A-M et al. (1998) *Microbiology* 144:433–439), *Streptococcus pyogenes*, and *Staphylococcus aureus*. All three homologs share the catalytic triad of the *E. coli* DegP protein.

The first identified in vivo target for DegP was colicin A lysis protein (Cal) (Cavard, D., Lazdunski, C. and Howard, S. P. (1989) *J. Bacteriol.* 171,6316–6322). DegP was found to degrade the acylated precusor form of Cal into two fragments. Mature Cal also accumulated to higher levels in degP mutant strains (Cavard et al.(1989), supra). A second family of DegP targets was identified as bacterial pilins. The K88 and K99 pilin subunits were found to accumulate to higher levels in degP mutant strains (Bakker, D., et a. (1991) *Mol. Microbiol.* 5,875–886). A more detailed study of this phenomenon demonstrated that P pilins, specifically PapA, are substrates for the DegP protease (Jones, C. H., et aL (1997) *EMBO J.* 16,6394–6406). More recently the *H. influenzae* non-pilus adhesin proteins HMW1 and HMW2 were found to be in vivo substrates for DegP (St. Geme III, J. W. and Grass, S. (1998) *Mol. Microbiol* 27,617–630).

The DegP/HtrA sequence was published in 1988 (Lipinska, Sharma, & Georgopoulos, supra). HtrA is one of several dozen proteases in *E coli* and is known to have homologs in cyanobacteria, mycobacteria, yeast and man (Pallen & Wren, supra). There are also two homologs of DegP: DegQ and DegS in *E coli* (Kolmar et al. (1996), supra; Waller, P. R. and Sauer, R. T. (1996) *J. Bacteriol* 178,1146–1153). A new homology region has recently been identified in DegP that is conserved in many eukaryotic proteins (Pallen & Wren, supra). Downstream from the catalytic sequence-208GNSGGAL214 are two PDZ domains (Levchenko, I., et al. (1997) *Cell* 91,939–947). These 80–100 amino acid domains are found in nearly 100 proteins, mostly eukaryotic, and probably play roles in protein-protein interactions, either facilitating multimer formation or substrate binding (Levchenko, I., et al. (1997), supra). The PDZ domain homology is maintained in the recently identified Gram-positive DegP homologs. Interestingly, Kolmar et al. (1996, supra) recently demonstrated that DegP forms dodecamers in vitro, although it remains to be seen if the PDZ domains contribute to DegP multimerization. If DegP does function as a multimer in vivo it would be reminiscent of the proteosome machines described in eukaryotic cytosol and ER (Pallen & Wren, supra).

Early in vivo data suggested that pilins were DegP substrates (Bakker, D., et al. (1991) supra). Expression of pilin subunit proteins in the absence of the chaperone resulted in failure to accumulate subunit in the periplasm and degP mutant strains accumulated more subunit in the periplasm (Bakker, D., et al. (1991), supra; Jones, et al. (1997) supra; Hultgren, S. J., Normark, S. and Abraham, S. N. (1991) *Annu. Rev. Microbiol* 45,383–415; Hultgren, S. J., Jones, C. H. and Normark, S. N. (1996) in *Escherichia coli and Salmonella; Cellular and Molecular Biology* (Neidhardt, F. C., eds) pp. 2730–2756, ASM Press Washington D.C.). Moreover, subunit expression in the degP mutant was highly toxic (Jones et al. (1997), supra). Both the toxicity and accumulation was suppressed by complementation with degP (Jones et al. (1997), supra. A significant obstacle to the study of pilus biogenesis is the inability to purify subunits in the absence of the PapD chaperone. This was overcome by the addition of an affinity tag to the amino-terminus of PapA. This provided for the purification of large quantities of PapA under denaturing conditions. Renaturation of PapA in the presence of the PapD chaperone allowed the formation of the PapD-PapA complex. Moreover, mixing DegP with denatured PapA resulted in affinity purification of a PapA-DegP complex and proteolysis with release of an amino-terminal PapA fragment.

SUMMARY OF THE INVENTION

Briefly, the present invention provides high through-put screening assays for the identification of inhibitors of DegP protease, an essential virulence factor in several human and non-human pathogens. The compounds identified by the present assay, small molecule inhibitors of DegP protease function, are expected to have high utility in the clinic.

With the foregoing and other objects, advantages and features of the invention that will become hereinafter apparent, the nature of the invention may be more clearly understood by reference to the following detailed description of the preferred embodiments of the invention and to the appended claims.

BRIEF DESCRIPTION OF THE DRAWINGS

FIG. 7A–7B Homology/consensus sequences for DegP-like proteases from gram-negative and gram-positive organisms. Thirty-six gram-negative and five gram-positive DegP homologs were selected, and the sequences for the catalytic domains (FIG. 7A) were separated from the sequences for the PDZ domains (FIG. 7B). Then, the sequences were aligned by hand in order to identify the consensus sequences. This provides a set of hallmarks for defining a DegP-like protease.

FIG. 8 shows an alignment of *E coli* DegP and three Gram-positive homologs. In this alignment, identical residues and conserved changes are shown in bold.

DETAILED DESCRIPTION OF THE PREFERRED EMBODIMENTS OF THE INVENTION

Figure 1A:
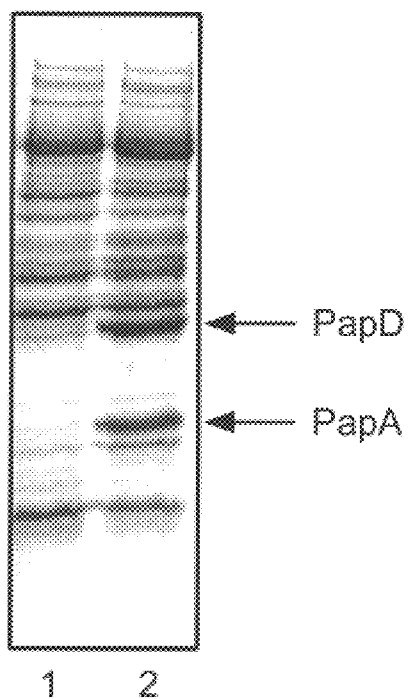
FIG. 1A–1C. Expression and purification of PapA-6his2ala and reconstitution of the PapD-PapA complex. A. Accumulation of PapA-6his4ala in the periplasm is dependent on the PapD chaperone. Periplasmic fractions from IPTG induction of PapA-6his4ala alone (lane 1) or co-induction of PapD chaperone and PapA-6his4ala (lane 2) in *E. coli* were prepared and loaded on SDS-PAGE. B. Purification of PapA-6his4ala-PapD complex from periplasm (lane 1, unbound material; lane 2, eluate). Metal affinity resin with bound complex was treated with 8M urea and washed to remove PapD. Eluted PapA-6his4ala is shown in lane 3. Lane 4 shows PapA-6his4ala eluate following dialysis to remove urea. The doublet PapA band in lane 3 is a result of urea treatment and proposed to be an altered form of the protein. C. Reconstitution of chaperone-subunit complex. Denatured PapA-6his2ala (lane 2) was mixed with purified PapD chaperone, allowed to bind to metal affinity resin, washed and eluted with 0.1M imidazole. The eluted complex is shown in lane 3. Lane 1 contains molecular weight standards. A, B, & C are SDS-PAGE (12.5%) stained with coomassie brilliant blue.

DegP is a periplasmic protease, present in many if not all Gram-negative bacteria, that is critical to bacterial viability and essential for pathogenesis, as DegP mutants do not survive in the host. The present invention is an in vitro assay for DegP activity. This assay utilizes a natural DegP substrate, the PapA pilin subunit, which is one of only two relevant substrates identified for DegP that are used in vitro, to result in an in vitro assay suitable for high through-put screening.

More particularly, the present invention relates to both a new antibiotic target and an assay to identify inhibitors of the target. The assay of the present invention is suitable for use in a high through-put assay for library screens. The assay components are the major pilin subunit of the Pap pilus immobilized on a resin and periplasmic extracts containing the DegP protease. Using the assay, the present inventors affinity-purified a complex containing PapA and DegP as well as a proteolytic amino-terminal fragment of PapA. In a preferred embodiment, all the components of the assay, including DegP protease and PapA target, are homogeneous preparations. Preferably, the target is reduced to a peptide containing the recognition/cleavage site. The peptide is then labeled with a detectable marker to monitor cleavage and/or a to monitor DegP activity. Utilization of this assay to screen inhibitor libraries is useful to identify small molecule compounds that inhibit DegP protease activity; these compounds will then be developed into therapeutically relevant drugs for the clinic.

In order to purify the protein to homogeneity, DegP may be cloned into a plasmid under the control of a well-regulated promoter. Using the proteolysis assay the PapA proteolytic products may be identified and sequenced to reveal the DegP cleavage site. Once the site is known a peptide will be designed and tested as a target for the protease. Finally, the peptide will be labeled with a detectable marker or configured for a fluorescence-proximity assay. This substrate will allow rapid analysis of proteolytic function and will be well suited for high-throughput screening ("HTS"). The present inventors have identified a DegP homolog in *Streptococcus pyogenes* and *Staphylococcus aureus;* therefore this protein is well represented in Gram-positive organisms, including the recently described homolog in *S. pneumoniae* (Gasc, A-M. et al. (1998) *Microbiology* 144:433–439).

Peptides may be labeled using any of a variety of labels and methods of labeling. Examples of types of labels which can be used in the present invention include, but are not limited to, enzyme labels, radioisotopic labels, non-radioactive isotopic labels, fluorescent labels, toxin labels, and chemiluminescent labels.

Examples of suitable enzyme labels include malate hydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, acetylcholine esterase, etc.

Examples of suitable radioisotopic labels include $^3$H, $^{125}$I, $^{131}$I, $^{32}$P, $^{35}$S, $^{14}$C, $^{51}$Cr, $^{57}$To, $^{58}$Co, $^{59}$Fe, $^{75}$Se, $^{152}$Eu, $^{90}$Y, $^{67}$Cu, $^{217}$Ci, $^{211}$At, $^{212}$Pb, $^{47}$Sc, and $^{109}$Pd.

Examples of suitable fluorescent labels include a $^{152}$Eu label, a fluorescein label, an isothiocyanate label, a rhodamine label, a phycoerythrin label, a phycocyanin label, and allophycocyanin label, an o-phthaldehyde label, an fluorescamine label, etc.

Examples of suitable toxin labels include diphtheria toxin, ricin, and cholera toxin. Examples of chemiluminescent labels include a luminal label, an isoluminal label, an aromatic acridinium ester label, and imidazole label, and acridinium salt label, an oxalate ester label, a luciferin label, a luciferase label, an aequorin label, etc.

Those of ordinary skill in the art will know of other suitable labels which may be employed in accordance with the present invention. The binding of these labels to antibodies or fragments thereof can be accomplished using standard techniques commonly known to those of ordinary skill in the art. Typical techniques are described by Kennedy, J. H., et al. *Clin. Chim. Acta* 70:1–31 (1976), and Schurs, A. H. W. M., et al, *Clin. Chim. Acta* 81:1–40 (1977). Coupling techniques mentioned in the latter are the glutaraldehyde method, the periodate method, the dimaleimide method, the m-maleimidobenzyl-N-hydroxy-succinimide ester method, all these methods incorporated by reference herein.

The following examples are presented in order to more fully illustrate the preferred embodiments of the invention. They should in no way be construed, however, as limiting the broad scope of the invention.

EXAMPLE 1

In the present Example, the inventors have used the assay of the present invention to purify a complex between DegP and PapA and a specific proteolysis fragment of PapA. The products of the assay/reaction are identified using amino acid sequencing.

Materials and Methods

Constructs

The PapA-6his and PapA-6his4ala were constructed by PCR as previously described (Morrison, H. G. and Desrosiers, R. C. (1993) *BioTechniques* 14,454–457) using the appropriate primers to create the desired insertions and restriction sites for ease of cloning. The complete PapA open reading frame was sequenced to assure that random mutations were not added during amplification. PapA-6his4ala was sub-cloned into pMMB66 (Furste, J. P., et al. (1986) *Gene* 48,119–131) under control of the IPTG inducible $P_{tac}$ promoter. PapD was expressed from pHJ9203, $P_{ara}$ promoter, as previously described (Jones, C. H., et al. (1997) *EMBO J.* 16,6394–6406). DegP was produced from pKS17 (see Strauch, K. L. et al. *J. Bact.* 171:2689–2696).

Expression and Purification of PapA-6his4ala

PapA-6his4ala was expressed along with PapD in KS474 (degP:kan) to provide for maximal translocation and stability in the periplasm. Induction conditions were 1 mM IPTG, 0.5% arabinose, 90 minutes, at A600=0.6–0.8. Periplasmic extracts were performed as previously described (Jones et al. (1997), supra) and dialyzed into 2 mM Tris, pH=8 to prepare for affinity purification. Talon metal affinity beads (Clontech, Palo Alto, Calif.) were used in batch per manufacturers instructions to purify PapA-6his4ala in complex with PapD. Elutions were performed by addition of 0.1M imidazole to the beads, rocking for 10 minutes and collecting supernatant. Three elutions were performed to maximize recovery. The complex, following dialysis, was denatured by addition of urea to 8M and reapplied to Talon resin. After washing in 10 mM Tris, pH=8/8M urea, pure PapA-6his4ala was eluted with 0.1M imidazole in 8M urea.

Co-purification of DegP and Proteolysis Assay

DegP was expressed from pKS17 by heat induction of the native heat inducible σE promoter (Lipinska et al., B., Sharma, S. and Georgopoulos (1988) *Nucleic Acids Research* 16,10053–10066). Periplasmic extracts were prepared as previously described (Jones et al. (1997), supra) and the periplasm dialyzed into 20 mM Tris, pH=8. DegP enriched and control (heat treated HB101) periplasm were added to PapA-6his4ala containing Talon resin (8M urea treated) and incubated at RT for 30 minutes with shaking. The Talon beads were extensively washed and then bound proteins were eluted with 0.1M imidazole.

Results

Construction of PapA-histidine Tag Fusion

A six-histidine affinity tagged PapA construct (PapA-6his) was constructed using PCR amplification. It was found that an alanine spacer had to be added between the histidine-tag (his-tag) and the leader peptidase cleavage point in PapA for efficient expression. When the his-tag was too close to the leader peptidase cleavage site PapA remained unprocessed and membrane associated (Jones, C. H., Liu, C. and Hultgren, S. J. (1998), supra ). A two-alanine spacer, making a total of four alanines between the histidine tag and the cleavage site, was placed between the his-tag (PapA-6his4ala) and the peptidase-processing site to overcome the proposed steric effect of the bulky histidine side chains. The PapA-6his-4ala derivative was properly leader processed and localized to the periplasm (FIG. 1).

Expression and Purification of PapA-6his-4ala Derivative

Figure 1C:
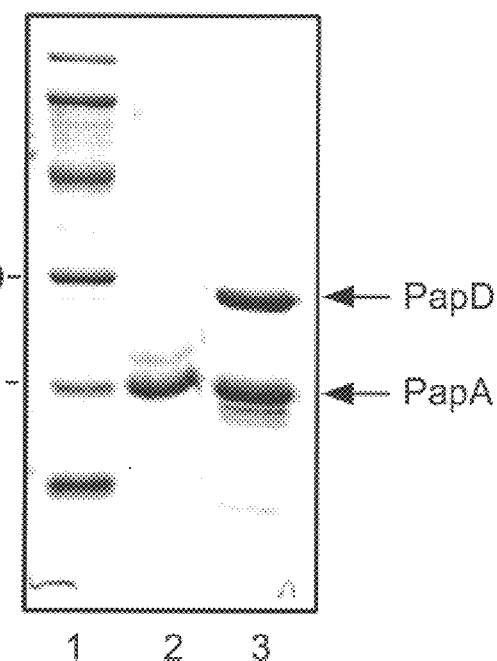
Figure 1B:
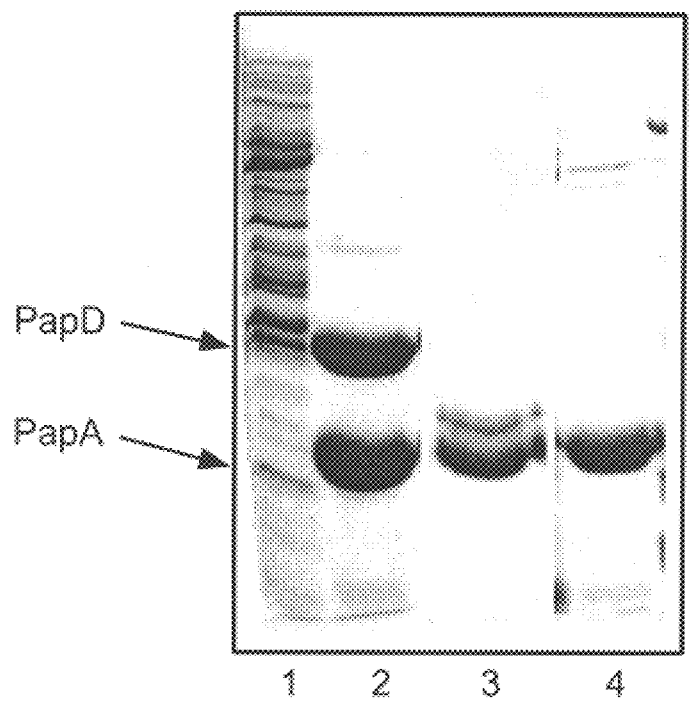

Pilin subunit accumulation in the periplasm is highly dependent on the periplasmic chaperone (Jones et al. (1997), supra). Therefore, the PapD chaperone was co-expressed with the affinity-tagged PapA. FIG. 1A illustrates that accumulation of PapA-6his4ala in the periplasm is dependent on PapD. Purification of PapA-6his4ala by affinity-chromatography on Talon metal-affinity resin (Clontech) resulted in co-purification of PapD in roughly equal molar amounts (FIG. 1B, lane2). In order to remove the PapD from the PapA-6his4ala, the Talon resin with bound complex was treated with 8 molar urea. The urea-washes contained virtually all of the PapD and little to none of the PapA-6his4ala, due to the fact that the metal affinity binding to poly-histidine is stable in 8M urea. Purified, denatured PapA-6his4ala could be purified by simple elution with 0.1M imidazole (FIG. 1B, lane 3). Chaperone-subunit complexes, PapD-PapA-6his4ala could be reformed in vitro by dilution of the resin-containing denatured PapA-6his4ala into either periplasm containing PapD or purified PapD. (FIG. 1C).

Purification of a PapA-6his4ala-DegP Complex

Figure 2:
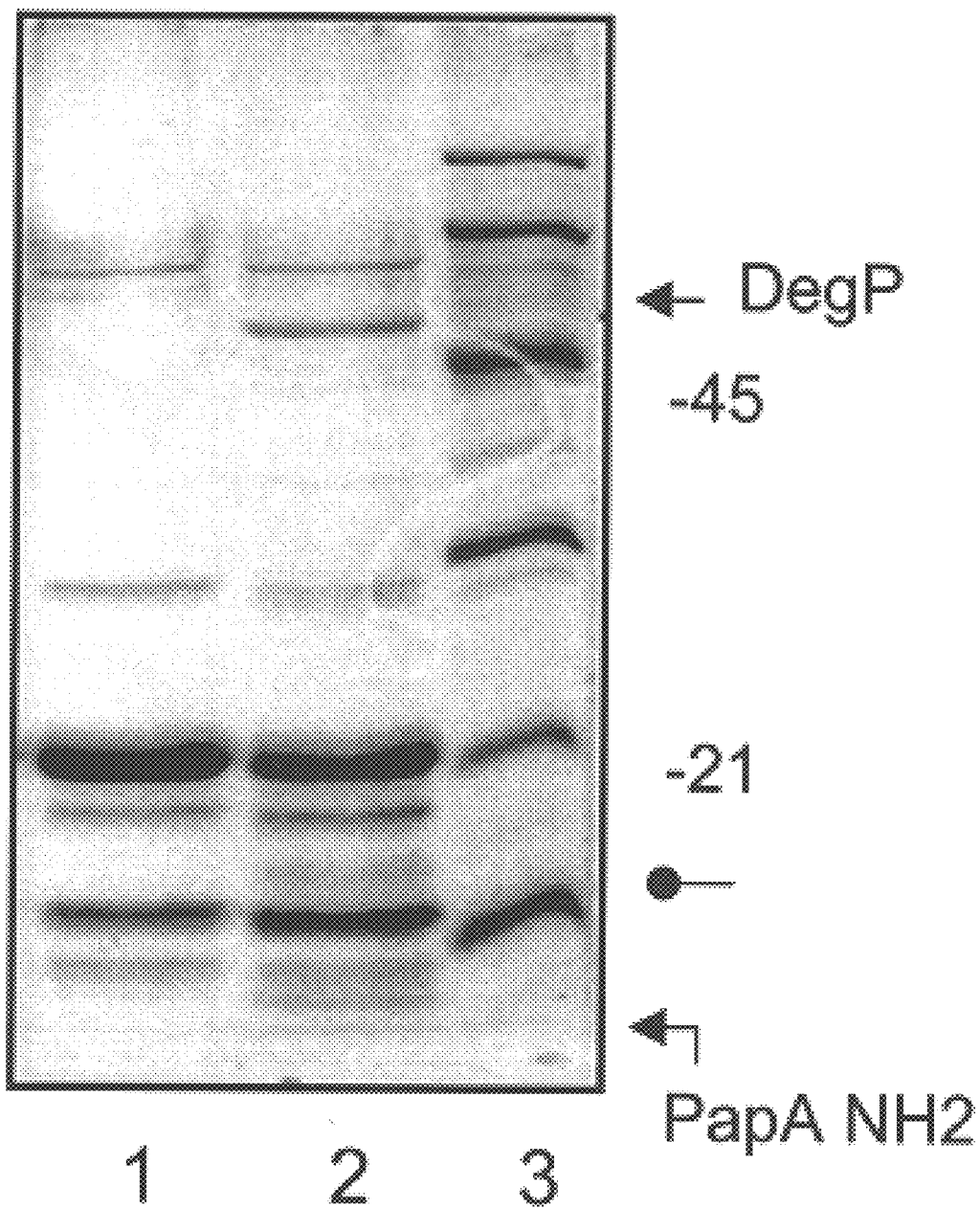
FIG. 2. DegP protease binding and cleavage of PapA-6his4ala. Denatured PapA-6his4ala linked to metal affinity resin was mixed with control periplasm (lane 1) or periplasm enriched with DegP (lane 2). Bound protein was eluted from the metal affinity resin with 0.1M imidazole. The eluates were then run on SDS-PAGE and stained with coomassie brilliant blue. The 3 novel bands that appear in lane 2 (DegP enriched) and not in lane 1 (control periplasm) are indicated. The round arrow indicates a new band that has not yet been identified. The DegP and PapA-NH2 bands were verified by amino acid sequencing. The sequence for the DegP band was identical to that published by Lipinska et al. (1988; supra) AETSSA. The amino terminal sequence of the 12kDa PapA-NH2 band was AAAHHHH, confirming that signal processing occurred at the correct site; the 4 histidines are part of the 6-histidine tag.

Addition of DegP containing periplasm to the denatured PapA-6his4ala resin, mixing 30 minutes at room temperature and elution of bound material revealed several new bands in addition to PapA-6his4ala, one of which is approximately 48 kDa (FIG. 2, lane 2). Amino-terminal sequencing identified the 48 kDa protein as Deg P, suggesting that the protease bound to the denatured PapA-6his4ala. In addition to the PapA-6his4ala and DegP proteins, two other proteins were eluted from the PapA-6his4ala affinity resin. The approximately 12 kDa band was found to have the 6his amino terminus of the PapA-6his4ala, suggesting that it represents an amino-terminal cleavage product of full length PapA-6his4ala (FIG. 2, lane 3).

Purification of DegP

Figure 3A:
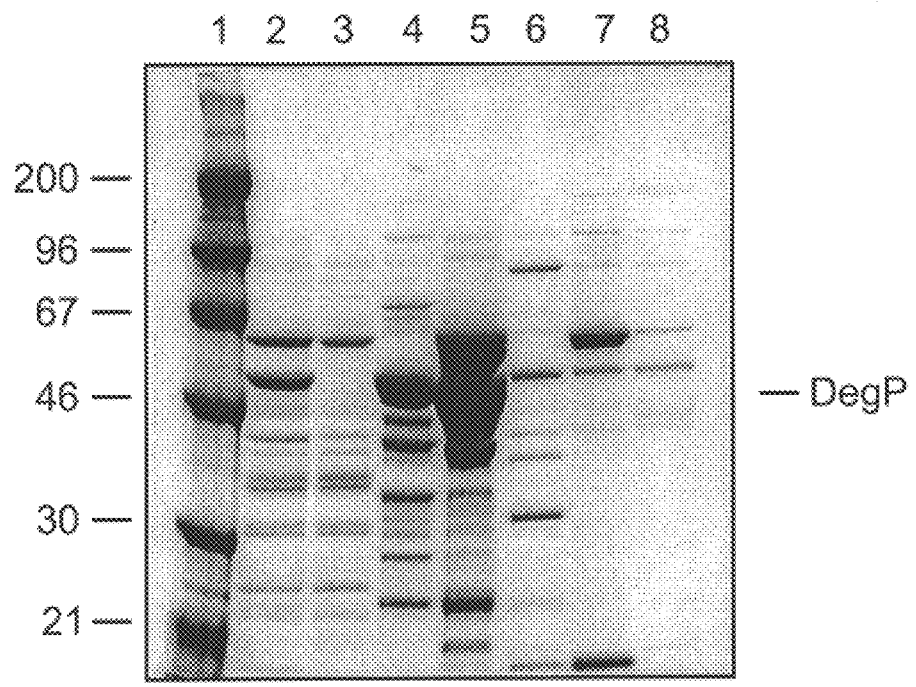
FIG. 3A–3B Purification of DegP. A. Cation exchange fractionation. Periplasm prepared from 30 grams of cells was applied to a 5 ml HiTrap SP column (Amersham-Pharmacia Biotech, Upsalla, Sweden) and eluted with a linear salt gradient. The starting material and flow through fraction are shown in lanes 2 and 3, respectively. The relevant portion of the elution gradient is shown in lanes 4–8. DegP eluted at approximately 100 mM NaCl. B. HIC butyl fractionation. Peak fractions from the cation exchange fractionation were pooled and applied to a HiTrap HIC butyl column (Pharmacia). The flow through fraction is shown in lane 2. DegP eluted in approximately 0.3M salt and is shown in lanes 4–8. The small arrows indicate truncated forms of DegP, all of which were identified by amino-terminal sequencing (unpublished data). In both A and B, lane 1 contains high molecular weight markers.
Figure 3B:
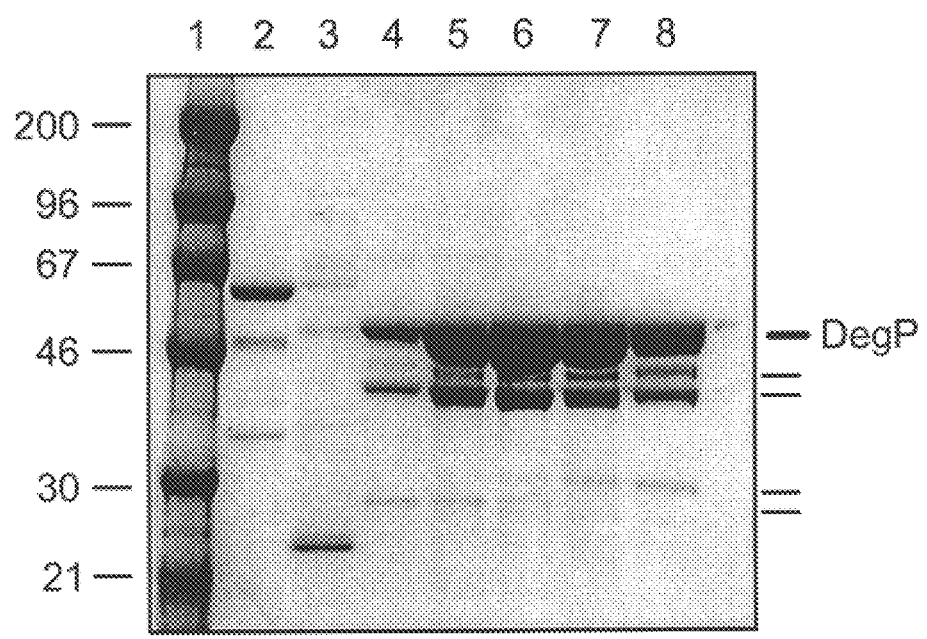

DegP protease was purified from whole periplasm prepared as previously described (Jones et al. (1997)). It was noted that increased yields of DegP were obtained from an overnight (saturated) culture as opposed to a transient heat shock (45° C.) of a mid-log culture. The periplasmic extract was dialyzed into 33 mM Mes, 33 mM HEPES, 33 mM acetate, pH=5.9 and applied to a HiTrapS, cation exchange, column (Pharmacia, Upsalla, Sweden). DegP eluted at approximately 100 mM NaCl in a linear gradient (FIG. 3A). The peak fractions from the S column were dialyzed against 20 mM Tris, pH=7.0/0.5M AmSO4 and applied to a HIC butyl column (Pharmacia, Upsalla, Sweden). DegP eluted from the HIC column in approximately 40% Buffer B (0.3M AmSO4). The Deg P appears to be >98% pure with the only contaminants being two DegP specific truncates that occur due to auto-cleavage.

Protease Assay—Casein Substrate

Figure 4:
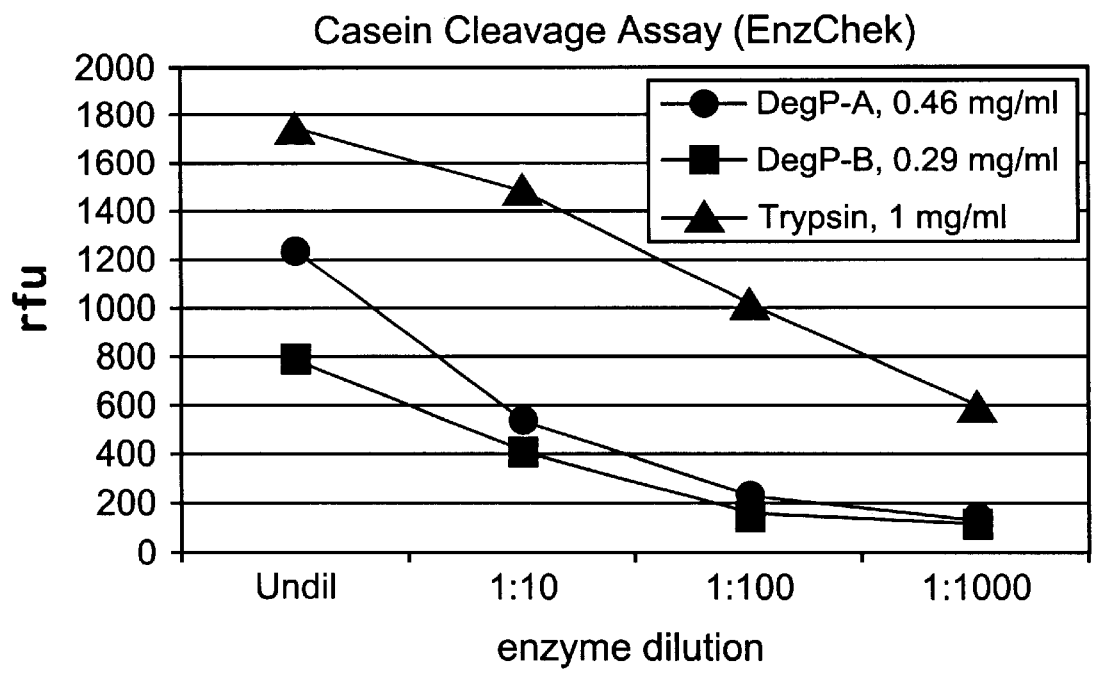
FIG. 4. DegP activity on casein substrate. A fluorescent casein substrate (Molecular Probes, Eugene, Oreg.) was used to screen for protease activity in the DegP fractions from the HIC purified material. Two separate preparations of DegP (degP-A, degP-B) were tested and shown to have activity comparable to the Trypsin control.

We used a commercial protease assay (EnzChek) to test for DegP activity on casein, which was previously observed (Lipinska et al., 1990). Heavily fluoresceinated (BODIPY) casein (Molecular Probes, Eugene, Oreg.) that is intramolecularly quenched is used as substrate and is a good target for detecting many types of proteases. Trypsin and DegP both cleave the casein substrate (FIG. 4). This assay was used to verify that the DegP that was eluted from each column purification step was active.

Soluble PapA Cleavage Assay

Figure 5:
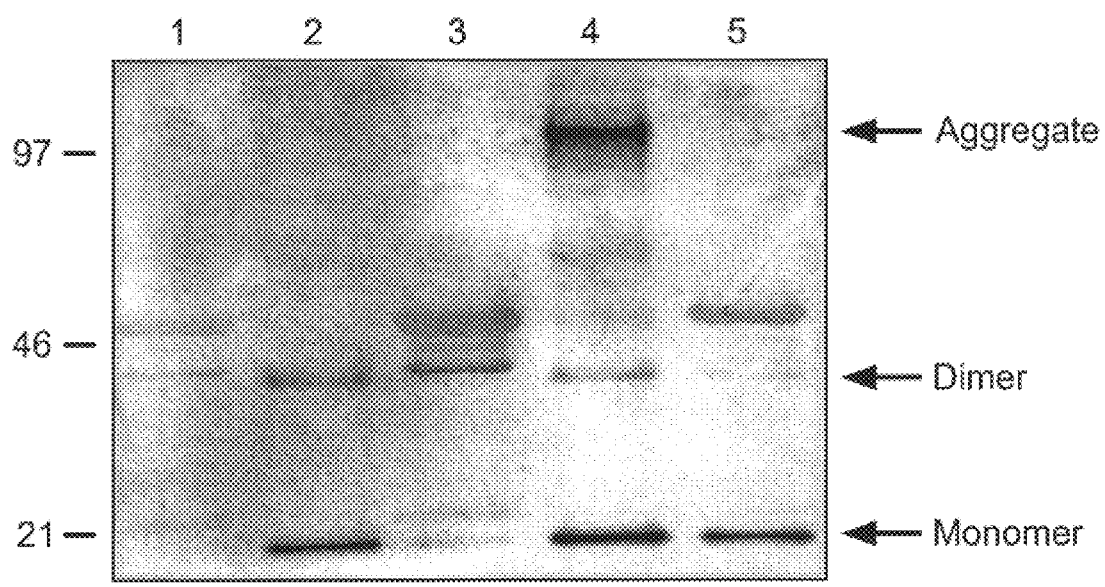
FIG. 5. In vitro DegP cleavage assay. Reduced and carboxymethylated PapA-6his4ala was mixed with DegP and incubated overnight at 45° C. The reactions were resolved on SDS-PAGE transferred to PVDF membrane and developed with a polyclonal antibody raised against whole P pili. PapA-6his4ala was incubated in the presence (lane 3—0.25 μg, lane 5—0.5 μg) and absence (lane 2—0.25 μg and lane 4—0.5 μg) of DegP, respectively. Lane 1 contains DegP alone as a control. Incubations were at 37° C. for 12 hours.

Purified DegP was tested on the PapA-6his4ala substrate under denaturing conditions. 20 μl of PapA-6his4ala (8M urea) was added to DegP (fraction 5 and 6 from the S column) in a final volume of 50 μl. The reaction was allwed to proceed overnight at 37° C. The experiment shown in FIG. 5 reveals two activities for DegP on the PapA substrate. In lanes 1–4 PapA has undergone limited degradation, as can be seen by the appearance of two novel bands around 12 kDa, similar to that seen in FIG. 2, and the decrease in the intensity of the full-length band when compared to lanes 5 and 6. The second activity appears to be blocking aggregate formation that appears only at pH-8. The reaction run in lanes 1, 2, and 5 were performed at pH=5.9, whereas the reactions run in lanes 3, 4, and 6 were performed at pH=8. DegP will also degrade PapA that has been denatured, reduced, carboxymethylated and dialyzed to remove urea as efficiently as the denatured substrate.

DegP Binding ELISA and Cleavage Assay

Figure 6:
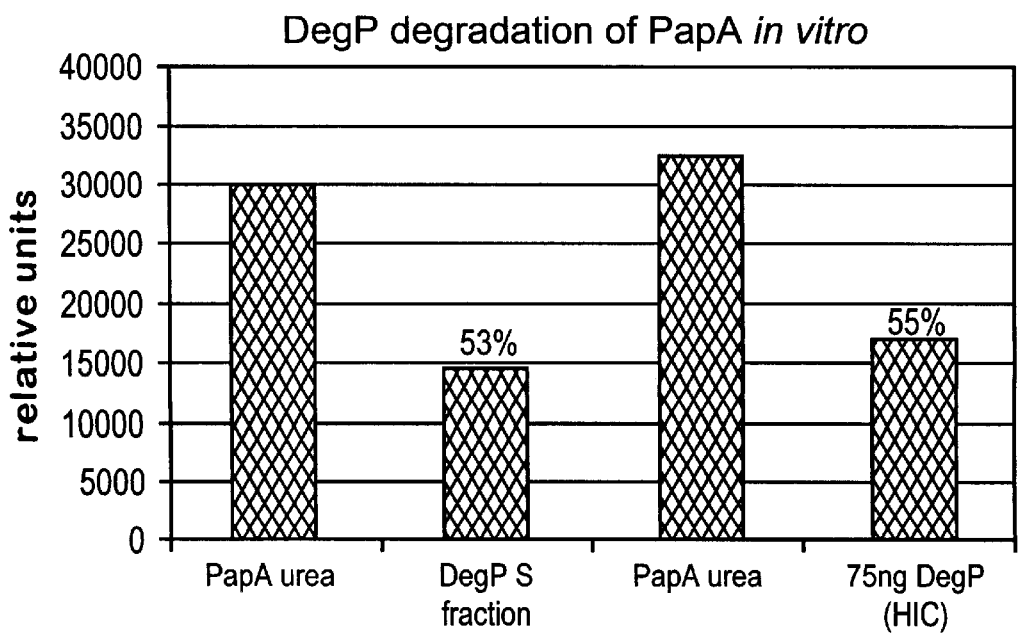
FIG. 6. DegP binding ELISA and high-throughput cleavage assay. A. Binding ELISA. PapA-6his4ala (0.8 mg/ml) was captured, using anti-6his antisera, on the wells of a 96 well microtiter plate. Serial five-fold dilutions of the protein preparation were applied in triplicate. DegP (50 pM) was added to the plate and incubated for 60 minutes. The ELISA was developed with anti-DegP antisera followed by alkaline-phosphatase conjugated goat-anti-rabbit secondary. B. Cleavage assay. PapA-6his4ala was captured as above and treated with DegP for two hours. Following washing the assay was developed with polyclonal anti-PapA antisera to detect PapA-6his4ala remaining on the plate.

Taking advantage of the 6-his affinity tagged PapA we designed a capture ELISA to detect DegP binding to PapA. The ELISA was modified to determine if, following incubation with DegP, a loss of PapA epitopes could be detected. Purified PapA6his4Ala was bound to the ELISA plate overnight. The plate was blocked with 3% BSA/1×PBS for 2 hours. DegP was then added to the plate for 1 hour and incubated at room temperature. The plate was washed in 1×PBS and developed with anti-DegP antisera. As shown in FIG. 6A, DegP bound efficiently to native PapA-6his4ala. Next, native PapA-6his4ala was captured via the 6-his affinity tag and exposed to DegP for two hours. The assay was otherwise set up as described above. The ELISA was then developed with anti-PapA polyclonal antisera. Clearly, as shown in FIG. 6B, DegP proteolyzed a significant amount of PapA.

EXAMPLE 2

Identification of Homologous Sequences

A BLAST (Basic Local Alignment Search Tool) search was conducted to look for DegP/HtrA homologs. The E. coli DegP was used as the query sequence in the search and each subject sequence found was aligned with E. coli DegP. Except for the Ricksettia sequences, all of the bacterial homologs contain the catalytic triad (FIG. 7A) and at least one PDZ domain (FIG. 7B). Many of the eucaryotic homologs have the triad and PDZ domains, although some share homology only through the PDZ domain.

FIG. 8 shows an alignment of E. coli DegP and three Gram-positive homologs. In this alignment, identical residues and conserved changes are shown in bold. The important residues in this alignment that are conserved are histidine 105 (E. coli residue 137-numbering includes signal sequence and starts with the longer S. pneumoniae sequence), aspartic acid 135 (167) and serine 210 (252) which make up the catalytic triad of the serine protease. The first PDZ domain starts at residue 304 (methionine) and continues to glycine 401. E. coli Deg. P contains a second PDZ domain that runs from glutamine 417 to aspartic acid 496. Given that this family of proteins is very large, these homologies are well preserved and fitted to structural motifs.

While the invention has been described and illustrated herein by references to various specific material, procedures and examples, it is understood that the invention is not restricted to the particular material, combinations of material, and procedures selected for that purpose. Numerous variations of such details can be implied and will be appreciated by those skilled in the art.

What is claimed is:

1. An assay for inhibitors of the DegP protease, comprising the steps of providing the major pilin subunit of the Pap pilus, the DegP protease, and a target peptide comprising the DegP recognition/cleavage site;

mixing DegP and a suitable substrate in the presence of a suspected inhibitor of DegP activity;

detecting the enzymatic activity of the DegP protease in the presence of the suspected inhibitor; and comparing the DegP activity in the presence of the inhibitor to the activity in the absence of the inhibitor.

2. An assay according to claim 1, wherein the major pilin subunit of the Pap pilus is immobilized on a solid substrate.

3. An assay according to claim 1, wherein the DegP protease is provided in the form of a periplasmic extract comprising the DegP protease.

4. An assay according to claim 1, wherein the suitable substrate of DegP is a natural substrate of DegP.

5. An assay according to claim 4, wherein said natural substrate of DegP is PapA pilin.

6. An assay according to claim 1, wherein all the components of the assay, including DegP protease and PapA target, are homogeneous preparations.

7. An assay according to claim 1, wherein the peptide containing the recognition/cleavage site is conjugated to a detectable label.

8. An assay according to claim 7, wherein the detectable label is a fluorescent dye.

* * * * *

SEQUENCE LISTING

```
<160> NUMBER OF SEQ ID NOS: 35

<210> SEQ ID NO 1
<211> LENGTH: 6
<212> TYPE: PRT
<213> ORGANISM: Escherichia coli
<220> FEATURE:
<221> NAME/KEY: PEPTIDE
<222> LOCATION: (6)
<223> OTHER INFORMATION: Amino acid 6 is xaa wherein xaa = any residue.

<400> SEQUENCE: 1

Gly Ser Gly Val Ile Xaa
 1               5

<210> SEQ ID NO 2
<211> LENGTH: 10
<212> TYPE: PRT
<213> ORGANISM: Escherichia coli
<220> FEATURE:
<221> NAME/KEY: PEPTIDE
<222> LOCATION: (3)..(4)
<223> OTHER INFORMATION: Amino acids 3 and 4 are xaa wherein xaa = any
      residue.
<221> NAME/KEY: PEPTIDE
<222> LOCATION: (10)
<223> OTHER INFORMATION: Amino acid 10 is xaa wherein xaa = Ala, Leu,
      Ile, Val.

<400> SEQUENCE: 2

Gly Tyr Xaa Xaa Thr Asn Asn His Val Xaa
 1               5                  10

<210> SEQ ID NO 3
<211> LENGTH: 8
<212> TYPE: PRT
<213> ORGANISM: Escherichia coli
<220> FEATURE:
```

```
<221> NAME/KEY: PEPTIDE
<222> LOCATION: (2)..(6)
<223> OTHER INFORMATION: Amino acids 2, 4 and 6 are xaa wherein xaa =
      any residue.

<400> SEQUENCE: 3

Ile Xaa Val Xaa Leu Xaa Asp Gly
 1               5

<210> SEQ ID NO 4
<211> LENGTH: 13
<212> TYPE: PRT
<213> ORGANISM: Escherichia coli
<220> FEATURE:
<221> NAME/KEY: PEPTIDE
<222> LOCATION: (2)..(12)
<223> OTHER INFORMATION: Amino acids 2, 4-6 and 12 are xaa wherein xaa =
      any residue.
<221> NAME/KEY: PEPTIDE
<222> LOCATION: (8)..(13)
<223> OTHER INFORMATION: Amino acids 8, 10-11 and 13 are xaa wherein xaa
      = Ala, Leu, Ile, Val.

<400> SEQUENCE: 4

Gly Xaa Asp Xaa Xaa Xaa Asp Xaa Ala Xaa Xaa Xaa Xaa
 1               5                  10

<210> SEQ ID NO 5
<211> LENGTH: 24
<212> TYPE: PRT
<213> ORGANISM: Escherichia coli
<220> FEATURE:
<221> NAME/KEY: PEPTIDE
<222> LOCATION: (1)..(2)
<223> OTHER INFORMATION: Amino acids 1 and 2 are xaa wherein xaa = Ala,
      Leu, Ile, Val.
<221> NAME/KEY: PEPTIDE
<222> LOCATION: (4)..(22)
<223> OTHER INFORMATION: Amino acids 4, 11-12, 16 and 22 are xaa wherein
      xaa = any residue.

<400> SEQUENCE: 5

Xaa Xaa Ala Xaa Gly Asn Pro Phe Gly Leu Xaa Xaa Thr Val Thr Xaa
 1               5                  10                  15

Gly Ile Val Ser Ala Xaa Gly Arg
            20

<210> SEQ ID NO 6
<211> LENGTH: 27
<212> TYPE: PRT
<213> ORGANISM: Escherichia coli
<220> FEATURE:
<221> NAME/KEY: PEPTIDE
<222> LOCATION: (9)..(20)
<223> OTHER INFORMATION: Amino acids 9, 15, 17, 19 and 20 are xaa
      wherein xaa = any residue.
<221> NAME/KEY: PEPTIDE
<222> LOCATION: (23)
<223> OTHER INFORMATION: Amino acid 23 is xaa wherein xaa = Ala, Leu,
      Ile, Val.
<221> NAME/KEY: PEPTIDE
<222> LOCATION: (22)
<223> OTHER INFORMATION: Amino acid 22 is xaa wherein xaa = Glu or Gln.

<400> SEQUENCE: 6

Ile Gln Thr Asp Ala Ala Ile Asn Xaa Gly Asn Ser Gly Gly Xaa Leu
 1               5                  10                  15

Xaa Asx Xaa Xaa Gly Xaa Xaa Ile Ile Asn Thr
            20                  25
```

```
<210> SEQ ID NO 7
<211> LENGTH: 9
<212> TYPE: PRT
<213> ORGANISM: Escherichia coli
<220> FEATURE:
<221> NAME/KEY: PEPTIDE
<222> LOCATION: (8)
<223> OTHER INFORMATION: Amino acid 8 is xaa wherein xaa = any residue.

<400> SEQUENCE: 7

Gly Ile Gly Phe Ala Ile Pro Xaa Asn
  1               5

<210> SEQ ID NO 8
<211> LENGTH: 6
<212> TYPE: PRT
<213> ORGANISM: Escherichia coli

<400> SEQUENCE: 8

Gly Ser Gly Val Ile Tyr
  1               5

<210> SEQ ID NO 9
<211> LENGTH: 10
<212> TYPE: PRT
<213> ORGANISM: Escherichia coli
<220> FEATURE:
<221> NAME/KEY: PEPTIDE
<222> LOCATION: (1)
<223> OTHER INFORMATION: Amino acid 1 is xaa wherein xaa = any residue.
<221> NAME/KEY: PEPTIDE
<222> LOCATION: (10)
<223> OTHER INFORMATION: Amino acid 10 is xaa wherein xaa = Ala, Leu,
      Ile, Val.

<400> SEQUENCE: 9

Xaa Tyr Ile Val Thr Asn Asn His Val Xaa
  1               5                  10

<210> SEQ ID NO 10
<211> LENGTH: 8
<212> TYPE: PRT
<213> ORGANISM: Escherichia coli
<220> FEATURE:
<221> NAME/KEY: PEPTIDE
<222> LOCATION: (2)..(6)
<223> OTHER INFORMATION: Amino acids 2, 4 and 6 are xaa wherein xaa =
      any residue.
<221> NAME/KEY: PEPTIDE
<222> LOCATION: (1)..(3)
<223> OTHER INFORMATION: Amino acids 1 and 3 are xaa wherein xaa = Ala,
      Leu, Ile, Val.

<400> SEQUENCE: 10

Xaa Xaa Xaa Xaa Leu Xaa Asp Gly
  1               5

<210> SEQ ID NO 11
<211> LENGTH: 13
<212> TYPE: PRT
<213> ORGANISM: Escherichia coli
<220> FEATURE:
<221> NAME/KEY: PEPTIDE
<222> LOCATION: (2)..(12)
<223> OTHER INFORMATION: Amino acids 2, 4, 5 and 12 are xaa wherein xaa
      = any residue.
<221> NAME/KEY: PEPTIDE
<222> LOCATION: (8)..(11)
<223> OTHER INFORMATION: Amino acids 8 and 11 are xaa wherein xaa = Ala,
      Leu, Ile, Val.
```

```
<400> SEQUENCE: 11

Gly Xaa Asp Xaa Xaa Ser Asp Xaa Ala Val Xaa Xaa Ile
 1               5                  10

<210> SEQ ID NO 12
<211> LENGTH: 24
<212> TYPE: PRT
<213> ORGANISM: Escherichia coli
<220> FEATURE:
<221> NAME/KEY: PEPTIDE
<222> LOCATION: (1)..(2)
<223> OTHER INFORMATION: Amino acids 1 and 2 are xaa wherein xaa = Ala,
      Leu, Ile, Val.
<221> NAME/KEY: PEPTIDE
<222> LOCATION: (6)..(23)
<223> OTHER INFORMATION: Amino acids 6, 10-12, 21 and 23 are xaa wherein
      xaa = any residue.

<400> SEQUENCE: 12

Xaa Xaa Ala Ile Gly Xaa Pro Leu Gly Xaa Xaa Xaa Thr Val Thr Gln
 1               5                  10                  15

Gly Ile Val Ser Xaa Leu Xaa Arg
            20

<210> SEQ ID NO 13
<211> LENGTH: 28
<212> TYPE: PRT
<213> ORGANISM: Escherichia coli
<220> FEATURE:
<221> NAME/KEY: PEPTIDE
<222> LOCATION: (15)..(20)
<223> OTHER INFORMATION: Amino acids 15, 17, 19 and 20 are xaa wherein
      xaa = any residue.
<221> NAME/KEY: PEPTIDE
<222> LOCATION: (22)
<223> OTHER INFORMATION: Amino acid 22 is xaa wherein xaa = Glu or Gln.
<221> NAME/KEY: PEPTIDE
<222> LOCATION: (23)
<223> OTHER INFORMATION: Amino acid 23 is xaa wherein xaa = Ala, Leu,
      Ile, Val.

<400> SEQUENCE: 13

Ile Gln Thr Asp Ala Ala Ile Asn Pro Gly Asn Ser Gly Gly Xaa Leu
 1               5                  10                  15

Xaa Asn Xaa Xaa Gly Xaa Xaa Ile Gly Ile Asn Ser
            20                  25

<210> SEQ ID NO 14
<211> LENGTH: 9
<212> TYPE: PRT
<213> ORGANISM: Escherichia coli
<220> FEATURE:
<221> NAME/KEY: PEPTIDE
<222> LOCATION: (2)
<223> OTHER INFORMATION: Amino acid 2 is xaa wherein xaa = Ala, Leu,
      Ile, Val.

<400> SEQUENCE: 14

Gly Xaa Gly Phe Ala Ile Pro Ser Asn
 1               5

<210> SEQ ID NO 15
<211> LENGTH: 10
<212> TYPE: PRT
<213> ORGANISM: Escherichia coli
<220> FEATURE:
<221> NAME/KEY: PEPTIDE
<222> LOCATION: (2)..(7)
```

```
<223> OTHER INFORMATION: Amino acids 2, 4 and 7 are xaa wherein xaa =
      any residue.
<221> NAME/KEY: PEPTIDE
<222> LOCATION: (10)
<223> OTHER INFORMATION: Amino acid 10 is xaa wherein xaa = Ala, Leu,
      Ile, Val.

<400> SEQUENCE: 15

Gly Xaa Val Xaa Arg Gly Xaa Leu Gly Xaa
 1               5                   10

<210> SEQ ID NO 16
<211> LENGTH: 6
<212> TYPE: PRT
<213> ORGANISM: Escherichia coli
<220> FEATURE:
<221> NAME/KEY: PEPTIDE
<222> LOCATION: (1)..(5)
<223> OTHER INFORMATION: Amino acids 1 and 5 are xaa wherein xaa = Ala,
      Leu, Ile, Val.
<221> NAME/KEY: PEPTIDE
<222> LOCATION: (2)..(4)
<223> OTHER INFORMATION: Amino acids 2-4 are xaa wherein xaa = any
      residue.

<400> SEQUENCE: 16

Xaa Xaa Xaa Xaa Xaa Ala
 1               5

<210> SEQ ID NO 17
<211> LENGTH: 6
<212> TYPE: PRT
<213> ORGANISM: Escherichia coli
<220> FEATURE:
<221> NAME/KEY: PEPTIDE
<222> LOCATION: (2)..(5)
<223> OTHER INFORMATION: Amino acids 2-5 are xaa wherein xaa = any
      residue.
<221> NAME/KEY: PEPTIDE
<222> LOCATION: (6)
<223> OTHER INFORMATION: Amino acid 6 is xaa wherein xaa = Ala, Leu,
      Ile, Val.

<400> SEQUENCE: 17

Gly Xaa Xaa Xaa Xaa Xaa
 1               5

<210> SEQ ID NO 18
<211> LENGTH: 22
<212> TYPE: PRT
<213> ORGANISM: Escherichia coli
<220> FEATURE:
<221> NAME/KEY: PEPTIDE
<222> LOCATION: (4)..(21)
<223> OTHER INFORMATION: Amino acids 4, 9-10, 15-16, 20-21 are xaa
      wherein xaa = any residue.
<221> NAME/KEY: PEPTIDE
<222> LOCATION: (8)..(22)
<223> OTHER INFORMATION: Amino acids 8, 17 and 22 are xaa wherein xaa =
      Ala, Leu, Ile, Val.

<400> SEQUENCE: 18

Ser Pro Ala Xaa Lys Ala Gly Xaa Xaa Xaa Gly Asp Val Ile Xaa Xaa
 1               5                  10                  15

Xaa Asn Gly Xaa Xaa Xaa
            20

<210> SEQ ID NO 19
<211> LENGTH: 5
<212> TYPE: PRT
```

```
<213> ORGANISM: Escherichia coli
<220> FEATURE:
<221> NAME/KEY: PEPTIDE
<222> LOCATION: (2)..(4)
<223> OTHER INFORMATION: Amino acids 2-4 are xaa wherein xaa = any
      residue.
<221> NAME/KEY: PEPTIDE
<222> LOCATION: (5)
<223> OTHER INFORMATION: Amino acid 5 is xaa wherein xaa = Ala, Leu,
      Ile, Val.

<400> SEQUENCE: 19

Leu Xaa Xaa Xaa Xaa
 1               5

<210> SEQ ID NO 20
<211> LENGTH: 10
<212> TYPE: PRT
<213> ORGANISM: Escherichia coli
<220> FEATURE:
<221> NAME/KEY: PEPTIDE
<222> LOCATION: (2)..(7)
<223> OTHER INFORMATION: Amino acids 2, 3, 5, 7 are xaa wherein xaa =
      any residue.
<221> NAME/KEY: PEPTIDE
<222> LOCATION: (4)..(9)
<223> OTHER INFORMATION: Amino acids 4, 8 and 9 are xaa wherein xaa =
      Ala, Leu, Ile, Val.

<400> SEQUENCE: 20

Gly Xaa Xaa Xaa Xaa Leu Xaa Xaa Xaa Arg
 1               5                  10

<210> SEQ ID NO 21
<211> LENGTH: 10
<212> TYPE: PRT
<213> ORGANISM: Escherichia coli
<220> FEATURE:
<221> NAME/KEY: PEPTIDE
<222> LOCATION: (2)..(7)
<223> OTHER INFORMATION: Amino acids 2-4 and 7 are xaa wherein xaa = any
      residue.
<221> NAME/KEY: PEPTIDE
<222> LOCATION: (10)
<223> OTHER INFORMATION: Amino acid 10 is xaa wherein xaa = Ala, Leu,
      Ile, Val.

<400> SEQUENCE: 21

Gly Xaa Xaa Xaa Arg Pro Xaa Leu Gly Xaa
 1               5                  10

<210> SEQ ID NO 22
<211> LENGTH: 5
<212> TYPE: PRT
<213> ORGANISM: Escherichia coli
<220> FEATURE:
<221> NAME/KEY: PEPTIDE
<222> LOCATION: (3)..(4)
<223> OTHER INFORMATION: Amino acids 3-4 are xaa wherein xaa = any
      residue.
<221> NAME/KEY: PEPTIDE
<222> LOCATION: (5)
<223> OTHER INFORMATION: Amino acid 5 is xaa wherein xaa = Ala, Leu,
      Ile. Val.

<400> SEQUENCE: 22

Asx Leu Xaa Xaa Xaa
 1               5

<210> SEQ ID NO 23
<211> LENGTH: 6
```

```
<212> TYPE: PRT
<213> ORGANISM: Escherichia coli
<220> FEATURE:
<221> NAME/KEY: PEPTIDE
<222> LOCATION: (1)..(3)
<223> OTHER INFORMATION: Amino acids 1 and 3 are xaa wherein xaa = Ala,
      Leu, Ile, Val.
<221> NAME/KEY: PEPTIDE
<222> LOCATION: (2)..(5)
<223> OTHER INFORMATION: Amino acids 2, 4 and 5 are xaa wherein xaa =
      any residue.

<400> SEQUENCE: 23

Xaa Xaa Xaa Xaa Xaa Val
 1               5

<210> SEQ ID NO 24
<211> LENGTH: 22
<212> TYPE: PRT
<213> ORGANISM: Escherichia coli
<220> FEATURE:
<221> NAME/KEY: PEPTIDE
<222> LOCATION: (1)..(21)
<223> OTHER INFORMATION: Amino acids 1, 2, 5, 6, 10, 11, 15, 16 and 21
      are xaa wherein xaa = any residue.
<221> NAME/KEY: PEPTIDE
<222> LOCATION: (17)..(22)
<223> OTHER INFORMATION: Amino acids 17 and 22 are xaa wherein xaa =
      Ala, Leu, Ile, Val.

<400> SEQUENCE: 24

Xaa Xaa Ala Ala Xaa Xaa Gly Leu Lys Xaa Xaa Asp Val Ile Xaa Xaa
 1               5                  10                  15

Xaa Asp Gly Lys Xaa Xaa
            20

<210> SEQ ID NO 25
<211> LENGTH: 8
<212> TYPE: PRT
<213> ORGANISM: Escherichia coli
<220> FEATURE:
<221> NAME/KEY: PEPTIDE
<222> LOCATION: (2)..(7)
<223> OTHER INFORMATION: Amino acids 2, 3, 4 and 7 are xaa wherein xaa
      = any residue.

<400> SEQUENCE: 25

Leu Xaa Xaa Xaa Leu Tyr Xaa His
 1               5

<210> SEQ ID NO 26
<211> LENGTH: 10
<212> TYPE: PRT
<213> ORGANISM: Escherichia coli
<220> FEATURE:
<221> NAME/KEY: PEPTIDE
<222> LOCATION: (1)..(9)
<223> OTHER INFORMATION: Amino acids 1, 5, 7-9 are xaa wherein xaa = any
      residue.
<221> NAME/KEY: PEPTIDE
<222> LOCATION: (4)..(6)
<223> OTHER INFORMATION: Amino acids 4 and 6 are xaa wherein xaa = Ala,
      Leu, Ile, Val.

<400> SEQUENCE: 26

Xaa Asp Thr Xaa Xaa Xaa Xaa Xaa Xaa Arg
 1               5                  10

<210> SEQ ID NO 27
<211> LENGTH: 5
```

```
<212> TYPE: PRT
<213> ORGANISM: Escherichia coli
<220> FEATURE:
<221> NAME/KEY: PEPTIDE
<222> LOCATION: (2)..(3)
<223> OTHER INFORMATION: Amino acids 2 and 3 are xaa wherein xaa = any
      residue.

<400> SEQUENCE: 27

Gly Xaa Xaa Gly Ala
 1               5

<210> SEQ ID NO 28
<211> LENGTH: 7
<212> TYPE: PRT
<213> ORGANISM: Escherichia coli
<220> FEATURE:
<221> NAME/KEY: PEPTIDE
<222> LOCATION: (2)..(7)
<223> OTHER INFORMATION: Amino acids 2, 3, 4 and 7 are xaa wherein xaa =
      Ala, Leu, Ile, Val.
<221> NAME/KEY: PEPTIDE
<222> LOCATION: (5)..(6)
<223> OTHER INFORMATION: Amino acids 5 and 6 are xaa wherein xaa = any
      residue.

<400> SEQUENCE: 28

Gly Xaa Xaa Xaa Xaa Xaa Xaa
 1               5

<210> SEQ ID NO 29
<211> LENGTH: 6
<212> TYPE: PRT
<213> ORGANISM: Escherichia coli
<220> FEATURE:
<221> NAME/KEY: PEPTIDE
<222> LOCATION: (4)..(5)
<223> OTHER INFORMATION: Amino acids 4 and 5 are xaa wherein xaa = any
      residue.

<400> SEQUENCE: 29

Pro Ala Ala Xaa Xaa Gly
 1               5

<210> SEQ ID NO 30
<211> LENGTH: 21
<212> TYPE: PRT
<213> ORGANISM: Escherichia coli
<220> FEATURE:
<221> NAME/KEY: PEPTIDE
<222> LOCATION: (3)..(18)
<223> OTHER INFORMATION: Amino acids 3, 4, 5, 7, 12, 15 and 18 are xaa
      wherein xaa = Ala, Leu, Ile, Val.
<221> NAME/KEY: PEPTIDE
<222> LOCATION: (6)..(20)
<223> OTHER INFORMATION: Amino acids 6, 9, 13, 14, 16, 17, 19 and 20 are
      xaa wherein xaa = any residue.

<400> SEQUENCE: 30

Gly Asp Xaa Xaa Xaa Xaa Xaa Asn Xaa Gln Pro Xaa Xaa Xaa Xaa Xaa
 1               5                  10                  15

Xaa Xaa Xaa Xaa Leu
             20

<210> SEQ ID NO 31
<211> LENGTH: 7
<212> TYPE: PRT
<213> ORGANISM: Escherichia coli
<220> FEATURE:
<221> NAME/KEY: PEPTIDE
```

```
<222> LOCATION: (1)..(5)
<223> OTHER INFORMATION: Amino acids 1, 2, 3 and 5 are xaa wherein xaa =
      Ala, Leu, Ile, Val.
<221> NAME/KEY: PEPTIDE
<222> LOCATION: (6)
<223> OTHER INFORMATION: Amino acid 6 is xaa wherein xaa = any residue.

<400> SEQUENCE: 31

Xaa Xaa Xaa Leu Xaa Xaa Arg
 1               5

<210> SEQ ID NO 32
<211> LENGTH: 234
<212> TYPE: PRT
<213> ORGANISM: Escherichia coli

<400> SEQUENCE: 32
```

Met Lys Lys Thr Thr Leu Ala Leu Ser Arg Leu Ala Leu Ser Leu Gly
 1               5                  10                  15

Leu Ala Leu Ser Pro Leu Ser Ala Thr Ala Ala Glu Thr Ser Ser Ala
                20                  25                  30

Thr Thr Ala Gln Gln Met Pro Ser Leu Ala Pro Met Leu Glu Lys Val
            35                  40                  45

Met Pro Ser Val Val Ser Ile Asn Val Glu Gly Ser Thr Thr Val Asn
    50                  55                  60

Thr Pro Arg Met Pro Arg Asn Phe Gln Gln Phe Phe Gly Asp Asp Ser
65                  70                  75                  80

Pro Phe Cys Gln Glu Gly Ser Pro Phe Gln Ser Ser Pro Phe Cys Gln
                85                  90                  95

Gly Gly Gln Gly Gly Asn Gly Gly Gln Gln Gln Lys Phe Met Ala
                100                 105                 110

Leu Gly Ser Gly Val Ile Ile Asp Ala Asp Lys Gly Tyr Val Val Thr
            115                 120                 125

Asn Asn His Val Val Asp Asn Ala Thr Val Ile Lys Val Gln Leu Ser
        130                 135                 140

Asp Gly Arg Lys Phe Asp Ala Lys Met Val Gly Lys Asp Pro Arg Ser
145                 150                 155                 160

Asp Ile Ala Leu Ile Gln Ile Gln Asn Pro Lys Asn Leu Thr Ala Ile
                165                 170                 175

Lys Met Ala Asp Ser Asp Ala Leu Arg Val Gly Asp Tyr Thr Val Gly
            180                 185                 190

Ile Gly Asn Pro Phe Gly Leu Gly Glu Thr Val Thr Ser Gly Ile Val
        195                 200                 205

Ser Ala Leu Gly Arg Ser Gly Leu Asn Ala Glu Asn Tyr Glu Asn Phe
    210                 215                 220

Ile Gln Thr Asp Ala Ala Ile Asn Arg Gly
225                 230

```
<210> SEQ ID NO 33
<211> LENGTH: 134
<212> TYPE: PRT
<213> ORGANISM: SaureushtrA

<400> SEQUENCE: 33
```

Val Gly Ser Gly Val Val Tyr Lys Lys Ser Gly Asp Thr Leu Tyr Ile
 1               5                  10                  15

Val Thr Asn Ala His Val Val Gly Asp Lys Glu Asn Gln Lys Ile Thr
                20                  25                  30

```
Phe Ser Asn Asn Lys Ser Val Val Gly Lys Val Leu Gly Lys Asp Lys
            35                  40                  45

Trp Ser Asp Leu Ala Val Val Lys Ala Thr Ser Ser Asp Ser Ser Val
 50                  55                  60

Lys Glu Ile Ala Ile Gly Asp Ser Asn Asn Leu Val Leu Gly Glu Pro
 65                  70                  75                  80

Ile Leu Val Val Gly Asn Pro Leu Gly Val Asp Phe Lys Gly Thr Val
                 85                  90                  95

Thr Glu Gly Ile Ile Ser Gly Leu Asn Arg Asn Val Pro Ile Asp Phe
                100                 105                 110

Asp Lys Asp Asn Lys Tyr Asp Met Leu Met Lys Ala Phe Gln Ile Asp
            115                 120                 125

Ala Ser Val Asn Pro Gly
            130

<210> SEQ ID NO 34
<211> LENGTH: 236
<212> TYPE: PRT
<213> ORGANISM: SpneumhtrA

<400> SEQUENCE: 34

Met Glu Ala Asn Met Lys His Leu Lys Thr Phe Tyr Lys Lys Trp Phe
  1               5                  10                  15

Gln Leu Leu Val Val Ile Val Ile Ser Phe Phe Ser Gly Ala Leu Gly
                 20                  25                  30

Ser Phe Ser Ile Thr Gln Leu Thr Gln Lys Ser Ser Val Asn Asn Ser
            35                  40                  45

Asn Asn Asn Ser Thr Ile Thr Gln Thr Ala Tyr Lys Asn Glu Asn Ser
 50                  55                  60

Thr Thr Gln Ala Val Asn Lys Val Lys Asp Ala Val Val Ser Val Ile
 65                  70                  75                  80

Thr Tyr Ser Ala Asn Arg Gln Asn Ser Val Phe Gly Asn Asp Asp Thr
                 85                  90                  95

Asp Thr Asp Ser Gln Arg Ile Ser Ser Glu Gly Ser Gly Val Ile Tyr
                100                 105                 110

Lys Lys Asn Asp Lys Glu Ala Tyr Ile Val Thr Asn Asn His Val Ile
            115                 120                 125

Asn Gly Ala Ser Lys Val Asp Ile Arg Leu Ser Asp Gly Thr Lys Val
            130                 135                 140

Pro Gly Glu Ile Val Gly Ala Asp Thr Phe Ser Asp Ile Ala Val Val
145                 150                 155                 160

Lys Ile Ser Ser Glu Lys Val Thr Thr Val Ala Glu Phe Gly Asp Ser
                165                 170                 175

Ser Lys Leu Thr Val Gly Glu Thr Ala Ile Ala Ile Gly Ser Pro Leu
            180                 185                 190

Gly Ser Glu Tyr Ala Asn Thr Val Thr Gln Gly Ile Val Ser Ser Leu
            195                 200                 205

Asn Arg Asn Val Ser Leu Lys Ser Glu Asp Gly Gln Ala Ile Ser Thr
            210                 215                 220

Lys Ala Ile Gln Thr Asp Thr Ala Ile Asn Pro Gly
225                 230                 235

<210> SEQ ID NO 35
<211> LENGTH: 238
<212> TYPE: PRT
<213> ORGANISM: Spyogeneshtra
```

-continued

```
<400> SEQUENCE: 35

Met Pro Ser Met Lys His Ile Leu Lys Ser Leu Ser Ile Leu Leu Ile
1               5                   10                  15

Gly Phe Leu Gly Gly Leu Ile Ala Ile Ile Thr Phe Asn Asn Leu Tyr
            20                  25                  30

Pro His Ser Pro Ser Lys Ile Asn Ser Gly Lys Ala Thr Thr Ser Asn
            35                  40                  45

Met Val Phe Asn Asn Thr Thr Asn Thr Thr Lys Ala Val Lys Ala Val
        50                  55                  60

Gln Asn Ala Val Val Ser Val Ile Asn Tyr Gln Asp Asn Pro Ser Ser
65                  70                  75                  80

Ser Leu Ser Asn Pro Tyr Thr Lys Leu Phe Gly Glu Gly Arg Ser Lys
                85                  90                  95

Glu Asn Lys Asp Ala Glu Leu Ser Ile Phe Ser Glu Gly Ser Gly Val
            100                 105                 110

Ile Tyr Arg Lys Asp Gly Asn Ser Ala Tyr Val Val Thr Asn Asn His
            115                 120                 125

Val Ile Asp Gly Ala Lys Arg Ile Glu Ile Leu Met Ala Asp Gly Ser
    130                 135                 140

Lys Val Val Gly Glu Leu Val Gly Ala Asp Thr Tyr Ser Asp Leu Ala
145                 150                 155                 160

Val Val Lys Ile Ser Ser Asp Lys Ile Lys Thr Val Ala Glu Phe Ala
                165                 170                 175

Asp Ser Thr Lys Leu Asn Val Gly Glu Val Ala Ile Ala Ile Gly Ser
            180                 185                 190

Pro Leu Gly Thr Gln Tyr Ala Asn Ser Val Thr Gln Gly Ile Val Ser
        195                 200                 205

Ser Leu Ser Arg Thr Val Thr Leu Lys Asn Glu Asn Gly Glu Thr Val
    210                 215                 220

Ser Thr Asn Ala Ile Gln Thr Asp Ala Ala Ile Asn Pro Gly
225                 230                 235
```